US008436212B2

(12) United States Patent
Broglio et al.

(10) Patent No.: US 8,436,212 B2
(45) Date of Patent: May 7, 2013

(54) PURIFICATION OF IMPURE HEXAMETHYLENEDIAMINES

(75) Inventors: Maria Ignez Broglio, Sao Paulo (BR); Daniel Amoros, Venissieux (FR); Jean Vannier, Saint Bonnet de Mure (FR); Dider Letourneur, Rixheim (FR)

(73) Assignee: Rhodia Operations, Aubervilliers (FR)

( * ) Notice: Subject to any disclaimer, the term of this patent is extended or adjusted under 35 U.S.C. 154(b) by 264 days.

(21) Appl. No.: 12/682,301

(22) PCT Filed: Oct. 3, 2008

(86) PCT No.: PCT/EP2008/063288
§ 371 (c)(1),
(2), (4) Date: Jul. 15, 2010

(87) PCT Pub. No.: WO2009/047219
PCT Pub. Date: Apr. 16, 2009

(65) Prior Publication Data
US 2010/0292511 A1   Nov. 18, 2010

(30) Foreign Application Priority Data
Oct. 11, 2007 (FR) ...................................... 07 07134

(51) Int. Cl.
*C07C 209/84* (2006.01)
(52) U.S. Cl.
USPC ........................................................ 564/498

(58) Field of Classification Search ................... 564/498
See application file for complete search history.

(56) References Cited

U.S. PATENT DOCUMENTS

| 3,017,331 | A | | 1/1962 | Campbell et al. |
| 3,121,671 | A | * | 2/1964 | Lassiter ........................ 203/94 |
| 5,192,399 | A | | 3/1993 | Sieja |
| 5,961,788 | A | * | 10/1999 | Ostermaier .................... 203/37 |
| 6,139,693 | A | * | 10/2000 | Bassler et al. ................. 203/49 |
| 6,252,115 | B1 | * | 6/2001 | Luyken et al. ................ 564/437 |
| 6,300,497 | B1 | * | 10/2001 | Rehfinger et al. ........... 540/605 |
| 6,348,630 | B1 | * | 2/2002 | Merk et al. ................... 564/498 |
| 7,060,819 | B2 | * | 6/2006 | Allgeier et al. .............. 540/484 |
| 7,147,757 | B2 | * | 12/2006 | Luyken et al. .................... 203/2 |
| 2003/0023083 | A1 | | 1/2003 | Luyken et al. |
| 2008/0319220 | A1 | | 12/2008 | Leconte |

FOREIGN PATENT DOCUMENTS
FR   2892118 A1   4/2007

OTHER PUBLICATIONS

International Search Report corresponding to PCT/EP 2008/063288 mailed on Jan. 22, 2009.

* cited by examiner

*Primary Examiner* — Brian J Davis
(74) *Attorney, Agent, or Firm* — Dentons US LLP

(57) ABSTRACT

Impure hexamethylenediamines and more particularly those hexamethylenediamines containing contaminating amounts of tetrahydroazepine (THA), or more generally contaminating amounts of imines, are purified by distillation carried out with a short retention time of the impure hexamethylenediamine in the distillation column; the hexamethylenediamine obtained has a very low concentration of THA.

10 Claims, No Drawings

PURIFICATION OF IMPURE HEXAMETHYLENEDIAMINES

CROSS-REFERENCE TO PRIOR APPLICATIONS

This application claims priority under 35 U.S.C. §119 of FR 0707134, filed Oct. 11, 2007, and is a continuation of PCT/EP 2008/063288, filed Oct. 3, 2008 and designating the United States (published in the French language on Apr. 16, 2009 as WO 2009/047219 A1; the title and abstract were also published in English), each hereby expressly incorporated by reference in its entirety and each assigned to the assignee hereof.

The present invention relates to a process for the purification of hexamethylenediamine.

It relates more particularly to a process for the purification of hexamethylenediamine by separation from the tetrahydroazepine or more generally from the imines present in the hexamethylenediamine.

Hexamethylenediamine is a major chemical intermediate used in particular as monomer in the manufacture of polymers, such as polyamides, or as intermediate in the synthesis of isocyanate compounds.

Hexamethylenediamine is obtained by hydrogenation of adiponitrile in the presence of catalysts comprising metal elements, such as nickel, cobalt, iron, rhodium or ruthenium.

During the process for the hydrogenation of adiponitrile, by-products are formed, more particularly imines and more particularly still tetrahydroazepine (hereinafter referred to by the symbol THA) of the following formula:

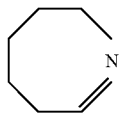

This compound has to be separated from the hexamethylenediamine as it can cause a coloration or connections in the polyamides, such as PA66, obtained with a hexamethylenediamine comprising tetrahydroazepine.

Numerous processes have been proposed for removing or separating the THA. These processes generally comprise the addition of a basic compound to promote the reaction of THA with hexamethylenediamine to form a new heavy compound or oligomer which can generally be separated from the hexamethylenediamine.

Thus, Patent U.S. Pat. No. 5,192,399 describes a process for the distillation of a hexamethylenediamine (HMD) and aminocapronitrile (ACN) mixture comprising THA. This mixture is distilled in a distillation column in the presence of a solution of a basic compound. The aminocapronitrile and the hexamethylenediamine are collected at the column top, while oligomers comprising the THA or heavy compounds are recovered in the bottom fraction of the column. The use of a basic compound generates saline effluents which cannot be discharged without treatment.

It is thus important to provide a process for the separation of the THA which makes it possible to recover hexamethylenediamine comprising a very low concentration of THA and with in particular very little generation of effluents to be discharged.

One of the aims of the present invention is to provide a simple process for the separation of hexamethylenediamine and tetrahydroazepine with recovery of the HMD comprising a very low concentration of THA and a minimalized loss of HMD.

To this end, the invention provides a process for the purification of hexamethylenediamine by separation from the tetrahydroazepine which consists in distilling, in a distillation column, the mixture comprising the hexamethylenediamine and the tetrahydroazepine. The invention is characterized in that the residence time of the hexamethylenediamine in the column is between one minute and twenty minutes, preferably between one minute and fifteen minutes.

The term "residence time in a distillation column" is understood to mean the ratio of the volume of liquid held in the column to the flow rate of liquid moving inside the column. In the case of the invention, the portion of the distillation column to be considered for the calculation of the residence time is the portion of the internal parts of the column situated above the feed point of the hexamethylenediamine to be purified. Thus, the residence times in the bottom of the column, in the boiler and in the condenser of the column are not to be taken into account. Likewise, the residence time in the internal parts present in the portion of the column situated below the feed point of the hexamethylenediamine is not to be taken into account. In other words, for the calculation of the residence time, the term "distillation column" used in the present text corresponds to the internal portion present in the portion of the column situated above the feed point of the hexamethylenediamine.

The term "internal parts present in the distillation column" is understood to mean the components or devices positioned in the column in order to promote and carry out the liquid/vapour exchange. Mention may be made, as examples of internal parts, of structured or unstructured packings, bubble cap plates, valve plates or the like. The internal parts composed of a structured packing are preferred in the process of the invention.

The volume of liquid held in the column depends on the type of internal parts, column, dimensions and operating conditions (gas and liquid flow rates in the column). Thus, for a packed column, the volume of liquid is calculated from the volume of packing and from the degree of retention of the packing (volume of liquid per unit of volume of packing). The volume of packing is, according to the invention, the volume present in the portion of the column situated above the feed point of the hexamethylenediamine. Generally, the degree of retention of a type of packing is indicated by the manufacturer or supplier of the packing and is a characteristic of the construction of this material and of the operating conditions of the distillation.

For a plate column, the volume of liquid held corresponds to the volume of liquid present on each plate multiplied by the number of real plates.

According to another characteristic of the invention, the process is implemented in distillation columns comprising between 10 and 50 theoretical plates, preferably between 15 and 35. This number of plates corresponds to the portion of the column situated above the feed point of the hexamethylenediamine.

The process of the invention can be implemented in any type of distillation column which makes it possible to obtain residence times as described above.

Advantageously, the distillation columns of the invention are those exhibiting a low pressure drop. Mention may be made, as type of distillation columns which are suitable, of structured packed columns or thin film distillation columns.

According to another characteristic of the invention, the process is implemented in distillation columns operating under an operating pressure in the column top of between 10 and 300 mbar. The column bottom temperature is advantageously between 120° C. and 170° C.

The mixture to be distilled is preferably fed at an intermediate plate of the column; the purified hexamethylenediamine recovered as top fraction or as intermediate fraction at a level close to the column top comprises, according to the process of the invention, less than 8 mol of THA per million mol of HMD, advantageously less than 4 mol of THA per million mol of HMD.

The concentration of THA or of impurities which can be reduced with a mercury electrode in the hexamethylenediamine is determined by assaying by differential pulse polarography. These impurities exhibit a polarographic wave of reduction at a voltage of −1.55 V/Ag-AgCl +/−0.05 V and are expressed in mmol of isobutanal per tonne of HMD (mmol iB/t) or in mol of THA per million mol of HMD (mpM).

Other details and advantages of the invention will become more clearly apparent in the light of the examples given below solely by way of indication.

EXAMPLE 1

In order to purify hexamethylenediamine comprising 120 mol of THA per million mol of HMD, use is made of a structured packed distillation column with a diameter of 50 mm comprising 2.6 litres of gauze packing with a degree of retention of 6%. This column exhibits a number of theoretical plates equal to 15. Feeding with hexamethylenediamine takes place below the bottom portion of the packing.

Distillation is carried out with a top pressure of 300 mbar, a column bottom temperature of 160° C. and an HMD feed flow rate of 2.5 kg/h (3.3 l/h). The liquid flow rate of the column is determined by calculation with the modelling tools conventionally used for the calculation of distillation columns (Aspen® software). The calculation shows that this flow rate is similar to the feed flow rate in the case of the present example.

The residence time of the hexamethylenediamine is 3 minutes.

The hexamethylenediamine collected at the column top comprises 2.3 mol of THA per million mol of HMD.

EXAMPLE 2

Example 1 is repeated, except that the packing used is a structured packing (not a gauze packing) with a degree of retention of 5% and a packing volume of 7 litres. The number of theoretical plates is 20.

The HMD residence time is 6 min. The hexamethylenediamine recovered at the column top comprises 2.9 mol of THA per million mol of HMD.

EXAMPLE 3

Example 1 is repeated. The packing volume is 3.6 l and the number of theoretical plates is equal to 20.

The HMD residence time in the column is 4 min. The hexamethylenediamine collected at the column top comprises 3.9 mol of THA per million mol of HMD.

COMPARATIVE EXAMPLE

In order to purify hexamethylenediamine comprising 120 mol of THA per million mol of HMD, use is made of a plate distillation column with a diameter of 50 mm comprising 30 real plates with a retention of 12 ml per plate. This column exhibits a number of theoretical plates equal to 17. The feeding of the hexamethylenediamine takes place below the bottom plate of the column.

Distillation is carried out with a top pressure of 260 mbar, a column bottom temperature of 160° C. and an HMD feed flow rate of 0.5 kg/h (0.66 l/h). The liquid flow rate of the column is determined by calculation with the modelling tools conventionally used for the calculation of distillation columns. The calculation shows that it is similar to the feed flow rate in the case of the present example.

The residence time of the hexamethylenediamine is 33 minutes.

The hexamethylenediamine collected at the column top comprises 16.4 mol of THA per million mol of HMD.

The invention claimed is:

1. A process for the purification of an impure hexamethylenediamine (HMD) containing tetrahydroazepine (THA) and/or other imines, comprising distilling, in a distillation column, the mixture which comprises the hexamethylenediamine and the tetrahydroazepine/imines, the residence time of the mixture in the distillation column ranging from one minute to twenty minutes.

2. The purification process as defined by claim 1, said residence time ranging from one minute to fifteen minutes.

3. The purification process as defined by claim 1, wherein the number of theoretical plates of the distillation column ranges from 10 to 50.

4. The purification process as defined by claim 1, wherein the distillation column bottom temperature ranges from 120° C. to 170° C.

5. The purification process as defined by claim 1, the purified hexamethylenediamine comprising less than 8 mol of THA per million mol of HMD.

6. The purification process as defined by claim 5, the purified hexamethylenediamine comprising less than 4 mol of THA per million mol of HMD.

7. The purification process as defined by claim 1, carried out in a packed distillation column.

8. The purification process as defined by claim 1, carried out in a plate distillation column.

9. The purification process as defined by claim 1, carried out in a thin film distillation column.

10. The purification process as defined by claim 1, the operating pressure at the column top ranging from 10 to 30 mbar.

* * * * *